United States Patent [19]

de Ruiter

[11] Patent Number: Plant 6,244

[45] Date of Patent: Aug. 9, 1988

[54] MINIATURE ROSE PLANT NAMED 'RUIFORTO'

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 888,152

[22] Filed: Jul. 22, 1986

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Charles W. Rummler

[57] ABSTRACT

A new variety of miniature rose characterized by its dwarf, compact, free blooming growth habit, producing brilliant coral-red blooms; the plant reaching a height of about 30 cm., and having a fast growth rate and abundant foliage.

1 Drawing Sheet

BACKGROUND OF THE NEW PLANT

My new variety of rose plant is the result of breeding efforts carried on by me at Hazerswoude, Holland, with the object of producing a miniature rose suitable for use as a flowering pot plant, as well as being useful for a garden decoration. This plant originated as a seedling derived by my crossing of an unnamed seedling with the variety 'Ruiredro', an unpatented variety, at my greenhouse breeding facilities in Holland. The form and beauty of the flowers of this new plant and its very fine growth habit led me to propagate this plant through several generations, by budding, which showed that the novel characteristics of this plant would hold true from generation to generation and appeared to be firmly fixed. Commercial propagation of this plant, by budding, is now being carried on under my direction at Hazerswoude, Holland.

DESCRIPTION OF THE DRAWING

My new variety of rose plant is illustrated by the accompanying photographic drawing, which shows the vegetative growth and flowers of this variety during July 1985. The specimens illustrated were grown with three plants in one pot in a greenhouse at Hazerswoude, Holland.

DESCRIPTION OF THE NEW PLANT

The following combination of characteristics is observed in the new variety:

(a) Readily propagated on its own roots by cuttings;

(b) Exhibits a well balanced, compact, vigorous growth habit which is extremely floriferous;

(c) Blooms carried mainly one per stem but often in clusters;

(d) Exhibits an excellent aptitude for greenhouse forcing as a flowering pot plant and also a very good comportment when used as an outdoor garden plant;

(e) Bloom color in general coral-red of a very long lasting quality.

Throughout this specification, colors are designated according to The R.H.S. Colour Chart published by The Royal Horticultural Society of London, England.

THE PLANT

Origin: Seedling.

Parentage:

*Seed parent.*—An unnamed variety.

*Pollen parent.*—'Ruiredro' (unpatented).

Classification:

*Botanic.*—Hybrid rose.

*Commercial.*—Miniature rose.

Form: Bush.

Habit: Upright and moderately branched.

Growth: Vigorous, upright and bushy.

Height: About 24 to 30 cm.

Foliage:

*Size.*—Small. Length — About 55–65 mm. Width — About 40–55 mm.

*Quantity.*—Normal, about 8 to 10 odd pinnate leaves.

*Number of leaflets.*—Normal mid-stem leaves, usually 5; occasionally 7.

*Color.*—New foliage — Yellow-Green, 147A. Old foliage — Green, 139A.

Leaflets:

*Shape.*—Elliptic to ovate.

*Texture.*—Firm.

*Margin.*—Serrated.

*Shape of base of terminal leaflet.*—Obtuse.

*Petiole.*—Color: Green under side with fine prickles.

*Stipules.*—Medium, fine, bearded.

Thorns:

*Quantity.*—On main canes from base — Very few. On laterals from main canes — Very few.

*Form.*—Concave, thin.

THE BUD

Form: Ovate.

Size:

*When sepals first divide.*—Small.

*Length.*—11 to 12 mm.

*Diameter.*—8 to 9 mm.

Color of petals:

*When sepals first divide.*—Red, 43A.

*When half blown.*—Upper side of petals — Red, 44B. Under side of petals — Red, 46C.

Sepals:

*Extensions.*—Absent in two, weak in three.

*Color.*—Green, 143A.

Receptacle:

*Shape.*—Pitcher shaped.

*Size.*—Small. Length — About 5 mm. Width — About 5 mm.

*Surface.*—Smooth.
*Color.*—Yellow-Green, 144A.
Peduncle:
*Length.*—About 76 mm.; slightly pubescent.
*Strength.*—Good.

THE FLOWER

Blooming habit: Continuous and abundant.
Borne: Singly; nearly no clusters.
Form:
*Upper part.*—Flattened convex.
*Under part.*—Flat.
*Size.*—Average open — 32 mm. to 38 mm.
Flower stems: About 34 to 41 mm. long.
Petals:
*Number.*—About 35 to 45.
*Arrangement.*—Generally impricated.
*Shape.*—Circular and with medium undulated margins.
*Texture.*—Thick, very firm.
*Color.*—Upper side of petals: Marginal Zone — Red, 43A. Middle Zone — Red, 41A. Basal Zone — Orange, 27D. Basal Spot — Yellow, 4D. Reverse side of petals: Marginal Zone — Red, 45C. Middle Zone — Red, 45D. Basal Zone — Red, 39C. Basal Spot — Yellow, 4D.
Discoloration: After two to three weeks, color becomes Red, 50A.

Variegations: Occasional white-greenish midrib.
Fragrance: None.
Persistence: Petals hang on and dry.
Lasting quality:
*On plant.*—More than three weeks.

REPRODUCTIVE ORGANS

Stamens:
*Anthers.*—Size: Small. Number: About 30 to 35. Color: Yellow-Orange, 22A.
*Filaments.*—Length: About 2 to 3 mm. Arrangement: Regular around the styles. Color: Orange, 25A.
*Pollen.*—Color: Greyed Orange, 164B.
Pistils:
*Number.*—About 30 to 35.
*Styles.*—Length: 5 to 6 mm. Color: Green, 139D.
*Stigmas.*—Color: Yellow-Green, 151D.
Character of ovaries: Normal.

I claim:

1. A new and distinct variety of rose plant of the miniature class, substantially as herein shown and described, characterized by the dwarf, compact, free blooming growth habit, producing brilliant coral-red blooms, approximately 38 millimeters in diameter, with petals of heavy substance; the plant being suitable as a pot plant as well as a garden decoration.

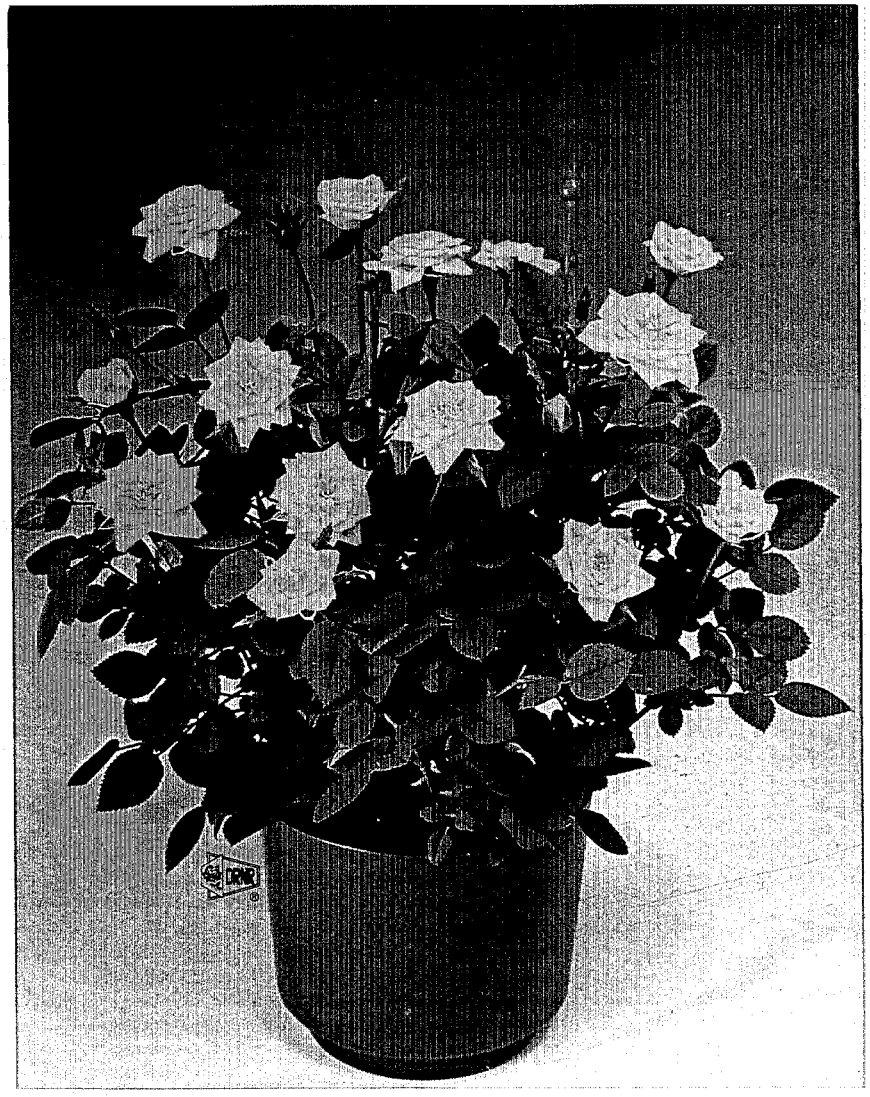

* * * * *